US010407397B2

(12) United States Patent
Royer et al.

(10) Patent No.: US 10,407,397 B2
(45) Date of Patent: Sep. 10, 2019

(54) METHOD FOR ISOLATION OF A DIANHYDRIDE AND DIANHYDRIDES PREPARED BY THE METHOD

(71) Applicant: SABIC Global Technologies B.V, Bergen op Zoom (NL)

(72) Inventors: Aaron Royer, Evansville, IN (US); Robert J. Werling, Evansville, IN (US); Jorge Jimenez, Lake Jackson, TX (US); Norman Enoch Johnson, Barrington, RI (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/096,080

(22) PCT Filed: Apr. 19, 2017

(86) PCT No.: PCT/US2017/028263
§ 371 (c)(1),
(2) Date: Oct. 24, 2018

(87) PCT Pub. No.: WO2017/189293
PCT Pub. Date: Nov. 2, 2017

(65) Prior Publication Data
US 2019/0119240 A1    Apr. 25, 2019

Related U.S. Application Data

(60) Provisional application No. 62/328,209, filed on Apr. 27, 2016.

(51) Int. Cl.
*C07D 307/89*    (2006.01)

(52) U.S. Cl.
CPC .................. *C07D 307/89* (2013.01)

(58) Field of Classification Search
CPC .................................................. C07D 307/89
USPC ....................................................... 549/350
See application file for complete search history.

(56) References Cited

U.S. PATENT DOCUMENTS

| | | |
|---|---|---|
| 3,389,970 A | 6/1968 | Scheibel |
| 3,875,116 A | 4/1975 | Heath et al. |
| 4,020,089 A | 4/1977 | Markezich |
| 4,116,980 A | 9/1978 | Webb |
| 4,217,281 A | 8/1980 | Markezich et al. |
| 4,257,953 A | 3/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,417,044 A | 11/1983 | Parekh |
| 4,520,204 A | 5/1985 | Evans |
| 4,571,425 A * | 2/1986 | Silva ................. C07C 51/567 548/454 |
| 4,584,388 A | 4/1986 | Webb |
| 4,902,809 A | 2/1990 | Groeneweg et al. |
| 5,359,084 A | 10/1994 | Dellacoletta et al. |
| 6,008,374 A | 12/1999 | Dellacoletta et al. |
| 6,235,866 B1 | 5/2001 | Khouri et al. |
| 6,265,521 B1 | 7/2001 | Fyvie et al. |
| 6,498,224 B1 * | 12/2002 | Odle .................. C08G 73/1007 528/125 |
| 7,153,394 B2 | 12/2006 | Guggenheim et al. |
| 2006/0205958 A1 | 9/2006 | Brunelle et al. |
| 2009/0056793 A1 | 3/2009 | Langhals et al. |
| 2011/0319620 A1 | 12/2011 | Ishihara et al. |
| 2019/0040201 A1 * | 2/2019 | Patil ....................... B29C 67/24 |
| 2019/0092726 A1 * | 3/2019 | Schulte, II ............. C09K 21/14 |
| 2019/0135750 A1 * | 5/2019 | Croll ................... B01D 11/0492 |

FOREIGN PATENT DOCUMENTS

| | | | |
|---|---|---|---|
| DE | 3213166 A1 | 10/1983 | |
| WO | WO-2017172593 A1 * | 10/2017 | ............. C09K 21/14 |

OTHER PUBLICATIONS

Schwartz; High Performance Polymers 1990, 2, 189-196. (Year: 1990).*
International Search Report for International Application No. PCT/US2017/028263; International Filing Date Apr. 19, 2017; dated Aug. 24, 2017; 6 pages.
Pinzow, Leonard, "Characteristics of a pulsed packed, liquid-liquid extraction column", Retrieved from teh internet on Sep. 20, 2018; http://hdl.handle.net/10945/13989; Jan. 1, 1957 pp. 1-105.
Rauber, Johannes, "Design Practice for Packed Liquid Liquid Extraction Columns", Retrieved from the Internet on Sep. 20, 2018; htt://folk.ntnu.no/skoge/prost/proceedings/aiche-2006/data/papers/P73337.pdf; Jan. 1, 2006 pp. 1-12.
Wei, Haibing et al., "Comparative Study on Polyimides from Isomeric 3,3'-, 3,4'-, and 4,4'—Linked Bis(thioetheranhydride)s", Journal of Polymer Science Part A: Polymer Chemistry, vol. 49, 2011: pp. 2484-2494.
Written Opinion of the International Searching Authority for International Application No. PCT/US2017/028263; International Filing Date Apr. 19, 2017; dated Aug. 24, 2017; 9 pages.
Yoon, Chong-Bok et al., "Facile synthesis of new NLO-functionalized polyimides via Mitsunobu reaction", Journal Material Chemistry, 1999, 9, pp. 2339-2344.

* cited by examiner

*Primary Examiner* — Daniel R Carcanague
(74) *Attorney, Agent, or Firm* — Cantor Colburn LLP

(57) ABSTRACT

A method for producing an aromatic dianhydride includes reacting an aromatic diimide with a substituted or unsubstituted phthalic anhydride in an aqueous medium in the presence of an amine exchange catalyst to provide an aqueous reaction mixture including an N-substituted phthalimide, an aromatic tetraacid salt, and at least one of an aromatic triacid salt and an aromatic imide diacid salt. The method further includes removing the phthalimide from the aqueous reaction mixture by extracting the aqueous reaction mixture with an organic solvent for a first time period, at a first extraction temperature and subsequent to the first time period, extracting the aqueous reaction mixture with an organic solvent for a second time period, at a second extraction temperature. The aromatic tetraacid salt is converted to the corresponding aromatic dianhydride. Aromatic dianhydrides prepared according to the method are also described.

20 Claims, 1 Drawing Sheet

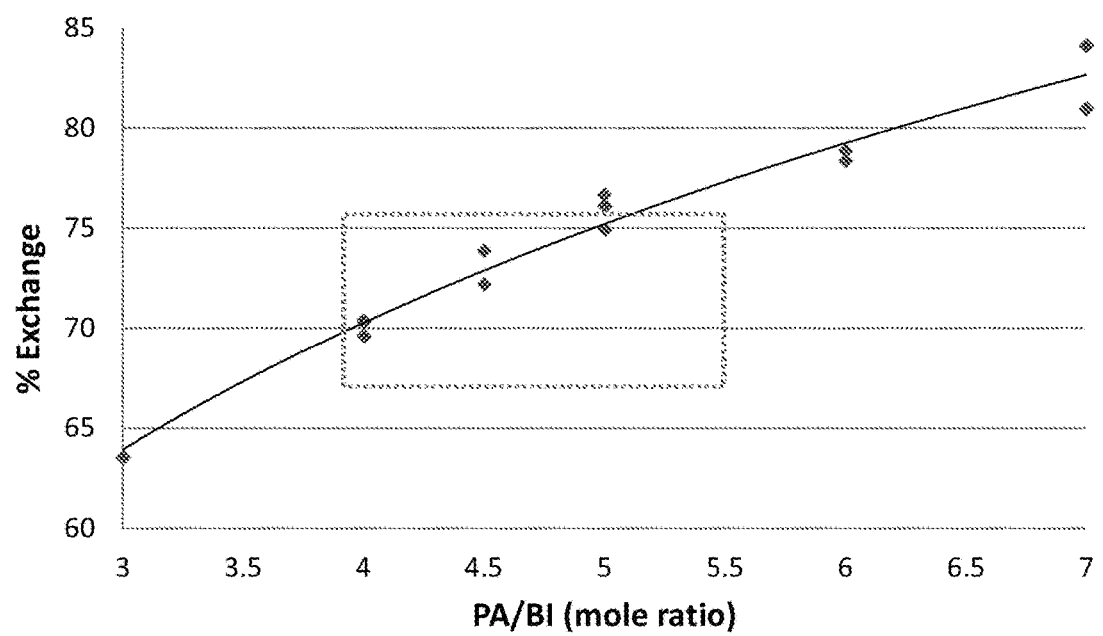

METHOD FOR ISOLATION OF A DIANHYDRIDE AND DIANHYDRIDES PREPARED BY THE METHOD

CROSS-REFERENCE TO RELATED APPLICATIONS

This application is a National Stage application of PCT/US2017/028263, filed Apr. 19, 2017, which claims the benefit of U.S. Provisional Application No. 62/328,209, filed Apr. 27, 2016, both of which are incorporated by reference herein in their entirety.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare various articles.

A number of processes for making polyetherimides have been disclosed. Two processes which have been of particular interest are the so-called melt polymerization and solution polymerization processes. Solution polymerization is generally conducted by reacting an aromatic dianhydride and an organic diamine in an inert solvent at elevated temperatures to form an amide-acid polymer via ring opening of the anhydride by nucleophilic attack of the diamine. The polyamide-acid is then formed into a polyetherimide by removal of water, for example by azeotropic distillation.

Aromatic dianhydrides are thus important to the production of polyetherimides. The aromatic dianhydrides can be prepared using an exchange reaction between an aromatic bisimide and a substituted or unsubstituted phthalic anhydride. In addition to dianhydride, the exchange reaction often produces various by-products which result in decreased yields of the dianhydride.

Accordingly, there remains a need for an improved method for producing and isolating dianhydrides that can provide high yields and minimize by-product formation.

BRIEF DESCRIPTION

A method for producing an aromatic dianhydride comprises reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig, preferably 200 to 250 psig; removing the phthalimide from the aqueous reaction mixture by extracting the aqueous reaction mixture with an organic solvent for a first time period, at a first extraction temperature that is 60 to 160° C., provided that the first extraction temperature is at least 10° C., preferably at least 20° C. or more preferably at least 30° C., or most preferably at least 40° C. lower than a maximum of the reaction temperature; subsequent to the first time period, extracting the aqueous reaction mixture with an organic solvent for a second time period, at a second extraction temperature that is 140 to 250° C., provided that the second extraction temperature is at least 5° C., preferably at least 10° C., more preferably at least 20° C. higher than the first extraction temperature; and converting the aromatic tetraacid salt to the corresponding aromatic dianhydride.

An aromatic dianhydride prepared by the method is also described.

The above described and other features are exemplified by the following FIGURE and detailed description.

BRIEF DESCRIPTION OF THE DRAWINGS

The following FIGURE is an exemplary embodiment.

The FIGURE shows the reaction conversion as percent exchange with respect to the phthalic anhydride to aromatic bisimide molar ratio.

DETAILED DESCRIPTION

The present inventors have discovered that use of a modified extraction procedure for isolation of an aromatic dianhydride can increase the overall dianhydride conversion and yield. The isolated aromatic dianhydrides advantageously have reduced amounts of imide anhydride by-products.

Accordingly, a method for producing an aromatic dianhydride represents one aspect of the present disclosure. The method comprises reacting an aromatic bisimide with a substituted or unsubstituted phthalic anhydride in an aqueous medium in the presence of an amine exchange catalyst and under conditions effective to provide an aqueous reaction mixture.

The aromatic bisimide can be of the formula (1)

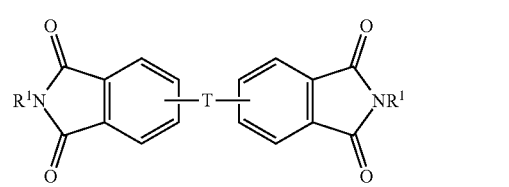

wherein T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing. In some embodiments, the R$^1$ is a monovalent C$_{1-13}$ organic group.

In some embodiments, T is —O— or a group of the formula —O—Z—O— wherein the divalent bonds of the —O— or the —O—Z—O— group are in the 3,3', 3,4', 4,3', or the 4,4' positions. Exemplary groups Z include groups of formula (2)

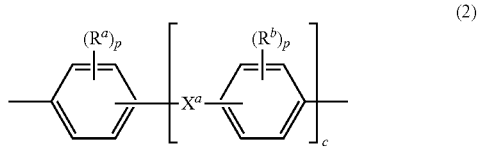

wherein R$^a$ and R$^b$ are each independently the same or different, and are a halogen atom or a monovalent C$_{1-6}$ alkyl group, for example; p and q are each independently integers of 0 to 4; c is 0 to 4; and X$^a$ is a bridging group connecting the hydroxy-substituted aromatic groups, where the bridging group and the hydroxy substituent of each C$_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of the formula (3a) or (3b)

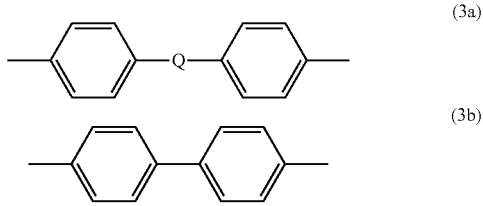

wherein Q is —O—, —S—, —C(O)—, —SO$_2$—, —SO—, —P(R$^a$)(=O)— wherein R$^a$ is a $C_{1-8}$ alkyl or $C_{6-12}$ aryl, or —C$_y$H$_{2y}$— wherein y is an integer from 1 to 5 or a halogenated derivative thereof (including a perfluoroalkylene group). Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In a specific embodiment, Z is derived from bisphenol A, such that Q in the above formula is, 2,2-isopropylidene. Thus in some embodiments, Z is 2,2-(4-phenylene)isopropylidene. In some embodiments, R$^1$ is a $C_{1-4}$ alkyl group, for example a methyl group, an ethyl group, a propyl group, or a butyl group, preferably a methyl group.

In some embodiments, the aromatic bisimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing.

The substituted or unsubstituted phthalic anhydride can be of the formula (4)

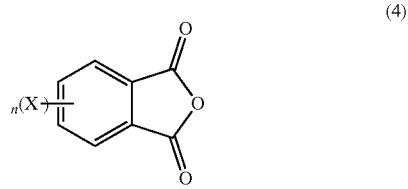

wherein X is fluoro, chloro, bromo, iodo, nitro, or a combination comprising at least one of the foregoing, and n is 0 or 1. In some embodiments, n is 0 and the phthalic anhydride is an unsubstituted phthalic anhydride. In some embodiments, n is 1, and the phthalic anhydride is a substituted phthalic anhydride, wherein X is fluoro, chloro, bromo, iodo, nitro, or a combination comprising at least one of the foregoing. In some embodiments, the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In an embodiment, the substituted or unsubstituted phthalic anhydride is preferably phthalic anhydride.

Reacting the aromatic bisimide with the substituted or unsubstituted phthalic anhydride is carried out in aqueous medium in the presence of an amine exchange catalyst. The amine exchange catalyst can include a ($C_{1-20}$ alkyl)-substituted amine, preferably a tri($C_{1-20}$ alkyl)amine. In some embodiments, the amine exchange catalyst is preferably triethylamine trimethylamine, or a combination comprising at least one of the foregoing. In some embodiments, the initial molar ratio of amine exchange catalyst to the phthalic anhydride is 1:1 to 2:1.

The reacting is further carried out under conditions effective to provide an aqueous reaction mixture. Effective conditions can include reacting at a reaction temperature that is 140 to 250° C., for example 160 to 200° C., and a reaction pressure of 150 to 300 psig (1.03 to 2.06 megapascals (MPa)), preferably 200 to 250 psig (1.37 to 1.72 MPa), more preferably 200 to 230 psig (1.37 to 1.58 MPa).

In some embodiments, the initial molar ratio of phthalic anhydride to aromatic bisimide is 4:1 to 20:1, or 4:1 to 10:1, or 4:1 to 8:1, or 4:1 to 5.5:1.

The aqueous reaction mixture provided by reacting the aromatic bisimide with the substituted or unsubstituted phthalic anhydride comprises an N-substituted phthalimide, an aromatic tetraacid salt, and at least one of an aromatic triacid salt and an aromatic imide diacid salt.

In some embodiments, the aromatic tetra acid salt is of the formula (5)

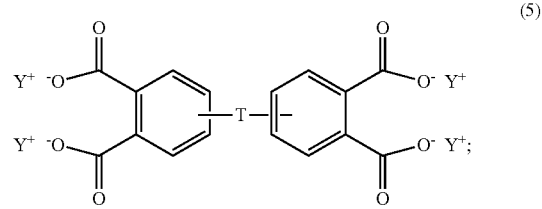

the aromatic triacid salt is of the formula (6)

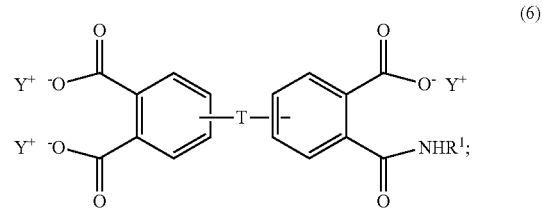

and
the aromatic imide-diacid salt is of the formula (7)

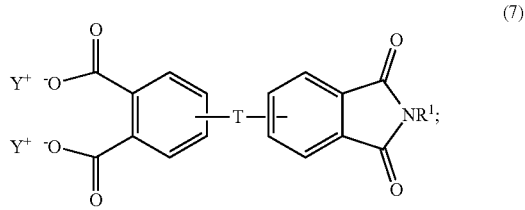

wherein T can be as described above, and is preferably —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing, R$^1$ is a C$_{1-13}$ organic group, or a C$_{1-4}$ alkyl group, preferably a methyl group, and Y is a cationic group, preferably a C$_{1-20}$ trialkylammonium group, or a proton (i.e., the aromatic tetraacid salt, triacid salt, and imide diacid salt can be in the form of the corresponding aromatic tetraacid, triacid, and imide acid, respectively). In some embodiments, Y is a C$_{1-20}$ trialkylammonium group, preferably a triethylammonium group. In some embodiments, T is —O—Z—O—, wherein Z is derived from bisphenol A. The divalent bonds of the —O—Z—O— group are in the 3,3', 3,4', 4,3', or the 4,4' positions.

In some embodiments, the aqueous reaction mixture can further comprise at least one of the aromatic bisimide and the substituted or unsubstituted phthalic anhydride.

The method further comprises removing the N-substituted phthalimide from the aqueous reaction mixture by extracting the aqueous reaction mixture with an organic solvent. The extracting to remove the phthalimide is preferably in an extraction column. When using an extraction column, the aqueous phase from the exchange reaction is typically fed into the top of the extraction column while the organic solution is fed into the bottom of the exchange column. In some embodiments, the volumetric ratio of the aqueous medium to the organic solvent is 0.3:1 to 3:1, or 0.5:1 to 1:1, or 0.75:1 to 1:1.

The extracting is carried out for a first period of time and at a first extraction temperature that is 60 to 160° C., or 60 to 150° C., provided that the first extraction temperature is at least 10° C., preferably at least 20° C., more preferably at least 30° C., most preferably at least 40° C. lower than a maximum reaction temperature. The present inventors have surprisingly discovered that use of the above defined first extraction temperature that is at least 10° C. lower than a maximum reaction temperature facilitates removal of the phthalimide. Advantageously, using the method described herein, loss of conversion of aromatic bisimide to aromatic dianhydride can be reduced or eliminated.

In some embodiments, the organic solvent is a (C$_{1-6}$ alkyl)benzene, benzene, or a halogenated aromatic solvent. For example, the organic solvent can comprise toluene, xylene, chlorobenzene, ortho-dichlorobenzene, or a combination comprising at least one of the foregoing. In some embodiments, the organic solvent is present in a volumetric ratio of aqueous medium to organic solvent of 0.3:1 to 3:1.

The first period of time can be, for example, 30 seconds to 3 hours, or 5 minutes to 3 hours, or 20 minutes to 3 hours, or 20 minutes to 2 hours, or 20 minutes to 1 hour, or 1 to 3 hours, or 1 to 2 hours, or 1 to 1.5 hours, preferably 5 minutes to 3 hours, or 20 minutes to 2 hours, or 20 minutes to 1 hour In some embodiments, at least 50%, at least 70%, at least 80%, or at least 90% of the phthalimide in the aqueous reaction mixture at the beginning of the first time period can be extracted into the organic solvent at the end of the first time period.

Subsequent to the first time period, the aqueous reaction mixture can be extracted with an organic solvent for a second time period and at a second extraction temperature that is 140 to 250° C., or 160 to 200° C., provided that the second extraction temperature is at least 5° C., preferably at least 10° C., more preferably at least 20° C. higher than the first extraction temperature. The present inventors have surprisingly discovered that use of the above defined second extraction temperature that is at least 5° C. higher than the first extraction temperature can provide improved conversion and ultimately higher yields for the dianhydride.

The second period of time can be, for example, 0.5 to 3 hours, or 0.5 to 2 hours, or 0.2 to 1.5 hours. In some embodiments, conversion of the aromatic bisimide to aromatic dianhydride can be greater than 70%, or greater than 75%, or greater than 78% or greater than 80% at the end of the second time period. In some embodiments, conversion of the aromatic bisimide to aromatic dianhydride can be 70 to 90%, or 75 to 90%, or 78 to 90%, or 80 to 90% at the end of the second time period.

In some embodiments, the extracting for the first time period and the second time period can be conducted in the same extractor. In some embodiments, the extracting for the first time period and the second time period can be conducted in different extractors. In some embodiments, the organic solvent can be provided to a second extractor to extract the aqueous reaction mixture for the second period of time and subsequently the same organic solvent from the second extractor can be used in a first extractor to extract the aqueous reaction mixture for the first period of time. For example, in a particular embodiment, the organic solvent recovered from the second extractor can be recycled for use in the first extractor. In some embodiments, the organic solvent can be simultaneously provided to both extractors, such that fresh organic solvent is used for each extraction. In some embodiments, a combination of fresh organic solvent and recycled organic solvent recovered from the outlet of one or both of the first and second reactors can be used for each extraction. For example, a combination of fresh organic solvent and recycled organic solvent recovered from the outlet of the second extractor and used in the first extractor can be used.

In some embodiments, the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing, and an organic stream comprising the organic solvent, N-substituted phthalimide, and optionally unreacted aromatic bisimide.

In some embodiments, the method can further include repeating the extracting to provide conversion of the aromatic bisimide to aromatic dianhydride at the end of the second time period in order to provide the desired conversion, for example greater than 70%, or greater than 75%, or greater than 78%, or greater than 80%. Repeating the extracting can include any number of additional extractions at either the first temperature or the second temperature, and in any order. For example, in some embodiments, the method can further comprise repeating the extracting for a first period of time and at a first extraction temperature. In some embodiments, the method can further comprise repeating the extracting for a first period of time and at a first extraction temperature, and subsequently repeating the extracting for a second period of time and at a second extraction temperature.

The method further comprises converting the aromatic tetraacid salt to the corresponding aromatic dianhydride. The amount of time as well as the temperature for the converting is generally dependent upon the identity of the dianhydride and can be readily determined by one of ordinary skill in the art. For example, useful temperatures can be 160 to 300° C., or 180 to 240° C. or 200 to 220° C. The conversion of the aromatic tetraacid salt to dianhydride is a cyclization with the concurrent formation of water. For example, the tetraacid salt can be condensed by refluxing in the presence of a dehydrating agent, for example acetic anhydride. In some embodiments, a temperature of 100 to 225° C. and a pressure of 0 MPa to 1 MPa can be used. The aromatic dianhydride can optionally be isolated using any isolation techniques that are generally known, for example, filtration. Advantageously, trace water, catalyst, and other residual volatile materials such as phthalic anhydride can also be removed as vapor under the conditions utilized for conversion. In some embodiments, the converting can provide a product mixture comprising the aromatic dianhydride and an aromatic imide-anhydride, for example formed from the cyclization of the above-described aromatic triacid salt.

The aromatic dianhydride can be of the formula (8)

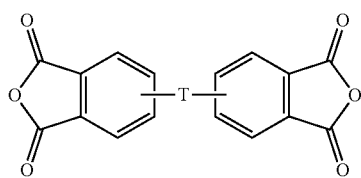

(8)

wherein T can be as defined above. In some embodiments, T is —O—Z—O—, preferably wherein Z is derived from bisphenol A (i.e., Z is 2,2-(4-phenylene)isopropylidene). Illustrative examples of aromatic dianhydrides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy) benzophenone dianhydride; and, 4-(2,3-dicarboxyphenoxy)-4'-(3,4-dicarboxyphenoxy)diphenyl sulfone dianhydride.

The aromatic imide-anhydride can be of the formula (9)

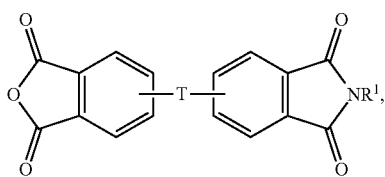

(9)

wherein T and $R^1$ are as defined above. In some embodiments, T is —O—Z—O—, wherein Z is derived from bisphenol A. In some embodiments, $R^1$ is preferably a methyl group.

The above-described method can be carried out as a batchwise method or a continuous method.

In a specific embodiment, the method comprises reacting an aromatic bisimide with a substituted or unsubstituted phthalic anhydride in an aqueous medium in the presence of an amine exchange catalyst at a reaction temperature that is 160 to 200° C. to form an aqueous reaction mixture; removing the phthalimide from the aqueous reaction mixture by extracting with an organic solvent at a first extraction temperature of 60 to 150° C., and subsequently extracting the aqueous reaction mixture with an organic solvent at a second extraction temperature that is 160 to 200° C.

An aromatic dianhydride prepared according to the above-described method is another aspect of the present disclosure. The aromatic dianhydride can be of formula (8) above. In some embodiments, the aromatic dianhydride can have an imide-anhydride content of less than or equal to 6 wt %, preferably less than or equal to 3 wt. %, more preferably less than or equal to 1 wt. %, even more preferably less than or equal to 0.1 wt %, based on the total weight of the aromatic dianhydride, wherein the imide-anhydride can be according to formula (9) above. The lower limit of the imide-anhydride content is not particularly limited, and can be, for example, as low as 0.0001 wt %, or as low as 0.001 wt %, or as low as 0.01 wt %, or as low as 0.1 wt %. In some embodiments, the imide-anhydride content of the aromatic dianhydride is undetectable by nuclear magnetic resonance (NMR) spectroscopy.

An improved method for isolation of an aromatic dianhydride is provided herein. The method advantageously employs extracting at carefully selected extraction temperatures in order to increase overall conversion to dianhydride and increase the yield of the isolated aromatic dianhydride. The aromatic dianhydride can include substantially reduced amounts of imide-anhydride by-product as compared to aromatic dianhydrides produced by methods that are currently known. Therefore, a substantial improvement in methods of isolating an aromatic dianhydride is provided.

The methods and aromatic dianhydrides prepared thereby are further illustrated by the following examples.

EXAMPLES

For each of the examples discussed below, the bisimide/dianhydride exchange reaction was carried out using the following general procedure. In a typical procedure, a reactor was charged with the aromatic bisimide (32.93 grams), phthalic anhydride (29.98 grams), and triethylamine (23.52 grams, in 113.5 grams of an aqueous solution comprising 15.1 wt. % triethylamine, and 13.0 wt. % phthalic anhydride, with the balance being water). The bisimide/dianhydride exchange reaction was carried out at 170° C. for 2 hours.

Comparative Example 1

To 199.1 grams of the above-described reaction mixture, 1.3 equivalents by weight, based on the weight of water, of toluene with 5 wt % triethylamine (96.1 grams) was added at a temperature of 170° C. to extract phthalimide and the corresponding aromatic bisimide. The mixture was maintained at 170° C. for 2 hours. The mixture was then cooled to 120° C. for 30 minutes, then to 70° C. for 30 minutes. The initial ratio of phthalic anhydride to bisimide was 4.99 to 1. Prior to the addition of toluene, conversion to dianhydride was 78.92%. Following the addition of toluene, conversion to dianhydride was 71.81%. The term "conversion" as used herein refers to (moles of dianhydride+½ moles imide anhydride) divided by (moles dianhydride+moles imide anhydride+moles aromatic bisimide).

Example 1

To 198.9 grams of the above-described reaction mixture, 1.06 equivalents by weight, based on the weight of water, of toluene with 5 wt % triethylamine (78.54 grams) was added at a temperature of 70° C. The reaction mixture was stirred at this temperature for 30 seconds, and the organic layer was decanted from the aqueous layer. This was repeated with 1.3 equivalents by weight based on the weight of water of toluene with 5 wt % triethylamine (94.6 grams, 94.1 grams) 2 more times. 1.3 equivalents by weight based on the weight of water of toluene with 5 wt % triethylamine (93.65 grams) was added at a temperature of 170° C. to further react imide anhydride and extract phthalimide and aromatic bisimide. The mixture was maintained at 170° C. for 1 hour. The initial ratio of phthalic anhydride to aromatic bisimide was 4.98 to 1. Prior to the extraction with toluene, conversion to dianhydride was 76.69%. Following the cold extraction procedure and hot reaction/extraction procedure, conversion to dianhydride was 86.96%. This represents a 13.4% increase in the overall conversion to the dianhydride.

Example 2

To 198.9 grams of the above-described reaction mixture, 0.65 equivalents by weight, based on the weight of water, of toluene with 5 wt % triethylamine (48.57 grams) was added at a temperature of 70° C. The reaction mixture was stirred for 30 seconds at this temperature, and the organic layer was decanted from the aqueous layer. This was repeated with 0.65 equivalents by weight based on the weight of water of toluene with 5 wt % triethylamine (48.9 grams, 48.1 grams) 2 more times. 1.3 equivalents by weight based on the weight of water of toluene with 5 wt % by weight triethylamine (96.0 grams) was added at a temperature of 170° C. to further react imide anhydride and extract phthalimide and aromatic bisimide. The mixture was maintained at 170° C. for 1 hour. The initial ratio of phthalic anhydride to aromatic bisimide was 4.98 to 1. Prior to the extraction with toluene, conversion to dianhydride was 78.84%. Following the extraction with toluene, conversion to dianhydride was 87.78%. This represents an 11.3% increase in the overall conversion to the dianhydride.

The cold extraction process can also be carried out in one or more steps, for example using one, two, or three consecutive extraction steps to increase the conversion to the dianhydride. The effect of using multi-step extractions is further demonstrated below with Comparative Examples 2 and 3, and Inventive Examples 3, 4, and 5.

Comparative Example 2

To 98.12 grams of a plant reactor sample comprising 6.34 wt % phthalimide, 12.92 wt % phthalic anhydride, 1.69 wt % aromatic bisimide, 5.21 wt % imide anhydride, 7.61 wt % dianhydride, 17.54 wt % triethylamine and 48.7 wt % water, 1.3 equivalents by weight based on the weight of water of toluene with 5 wt % triethylamine (62.11 grams) was added at a temperature of 170° C. to extract phthalimide and aromatic bisimide. The mixture was maintained at 170° C. for 2 hours. Prior to the extraction with toluene, conversion to dianhydride was 70.97%. Following the extraction with toluene, conversion to dianhydride was 71.20%. Thus the extraction with toluene at a temperature of 170° C. resulted in a 0.3% increase in the conversion to dianhydride.

Comparative Example 3

92.5 grams of the above-described plant reactor sample was stirred at 170° C. for 30 minutes, then 1.3 equivalents by weight based on the weight of water of toluene with 5 wt % triethylamine (60.17 grams) was added to extract phthalimide and aromatic bisimide. The mixture was maintained at 170° C. for 2 hours. Prior to the extraction with toluene, conversion to dianhydride was 76.13%. Following the extraction with toluene, conversion to dianhydride was 73.37%. Thus the extraction with toluene at a temperature of 170° C. resulted in a 2.76% decrease in the conversion to dianhydride.

Example 3

100.38 grams of the above-described plant reactor sample was stirred at 170° C. for 30 minutes, then 0.65 equivalents by weight, based on the weight of water, of toluene with 5 wt % triethylamine (31.81 grams) was added at a temperature of 70° C. The reaction mixture was stirred for 30 seconds and the organic layer was decanted from the aqueous layer. This was repeated with 0.65 equivalents by weight based on the weight of water of toluene with 5 wt % triethylamine (31.40 grams, 31.15 grams) at this temperature two more times. 1.3 equivalents by weight based on the weight of water of toluene with 5 wt % triethylamine (62.41 grams) was added at a temperature of 170° C. The mixture was maintained at 170° C. for 2 hours. Prior to the extraction with toluene, conversion to dianhydride was 76.07%. Following the extraction with toluene, conversion to dianhydride was 86.08%. This represents a 13.2% increase in the overall conversion to the dianhydride.

Example 4

105.37 grams of the above-described plant reactor sample was stirred at 170° C. for 30 minutes, then 0.65 equivalents by weight based on the weight of water of toluene with 5 wt % triethylamine (33.36 grams) was added at a temperature of 70° C. The reaction mixture was stirred for 30 seconds and the organic layer was decanted from the aqueous layer. This was repeated with 0.65 equivalents by weight, based on the weight of water, of toluene with 5 wt % triethylamine (33.02 grams) at this temperature. 1.3 equivalents by weight based on the weight of water of toluene with 5 wt % by weight triethylamine (65.25 grams) was added at a temperature of 170° C. The mixture was maintained at 170° C. for 2 hours. Prior to the extraction with toluene, conversion to dianhydride was 75.99%. Following the extraction with toluene, conversion to dianhydride was 83.96%. This represents a 10.5% increase in the overall conversion to the dianhydride.

Example 5

105.32 grams of the above-described plant reactor sample was stirred at 170° C. for 30 minutes, then 0.65 equivalents by weight based on the weight of water of toluene with 5 wt % triethylamine (33.36 grams) was added at a temperature of 70° C. The reaction mixture was stirred for 30 seconds and the organic layer was decanted from the aqueous layer once at this temperature. 1.3 equivalents by weight based on the weight of water of toluene with 5 wt % triethylamine (65.29 grams) was added at a temperature of 170° C. The mixture was maintained at 170° C. for 2 hours. Prior to the extraction with toluene, conversion to dianhydride was 75.95%. Following the extraction with toluene, conversion to dianhydride was 80.16%. This represents a 5.5% increase in the overall conversion to the dianhydride.

As demonstrated by Examples 3-5, the overall conversion to the desired dianhydride product is improved when the extraction process according to the present disclosure is used. Furthermore, Example 3 to 5 illustrate that the conversion to dianhydride can be improved by successive cold extractions steps. For example, three cold extractions (Example 3) resulted in an overall dianhydride conversion of 86.08%, two cold extractions (Example 4) resulted in an overall dianhydride conversion of 83.96%, and a single cold extraction (Example 5) resulted in an overall dianhydride conversion of 80.16%. In contrast, the Comparative Examples, using only extractions at 170° C. ("hot extraction") exhibited overall dianhydride conversions ranging from 71.20 to 73.37%. In some cases, the hot extraction procedure of the Comparative Examples resulted in a decrease in the overall conversion to dianhydride compared to the conversion prior to the extraction (Comparative Examples 1 and 3). Comparative Example 2 showed only a 0.3% percent improvement in conversion after extraction compared to the reaction mixture prior to extraction.

The conversion of the exchange reaction is also influenced by the ratio of the phthalic anhydride to the aromatic diimide. As shown in the FIGURE, the conversion (shown as "percent exchange") increases with increasing phthalic anhydride ("PA") to aromatic diimide ("BI") ratios. The preferred phthalic anhydride to aromatic bisimide ratios for the exchange reaction are 4:1 to 5.5:1.

The methods and aromatic dianhydrides of the present disclosure are further illustrated by the following non-limiting embodiments.

Embodiment 1: A method for producing an aromatic dianhydride, the method comprising reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig (1.03 to 2.06 MPa), preferably 200 to 250 psig (1.37 to 1.72 MPa); removing the phthalimide from the aqueous reaction mixture by extracting the aqueous reaction mixture with an organic solvent for a first time period, at a first extraction temperature that is 60 to 160° C., provided that the first extraction temperature is at least 10° C., preferably at least 20° C. or more preferably at least 30° C., or most preferably at least 40° C. lower than a maximum of the reaction temperature; subsequent to the first time period, extracting the aqueous reaction mixture with an organic solvent for a second time period, at a second extraction temperature that is 140 to 250° C., provided that the second extraction temperature is at least 5° C., preferably at least 10° C., more preferably at least 20° C. higher than the first extraction temperature; and converting the aromatic tetraacid salt to the corresponding aromatic dianhydride.

Embodiment 2: The method of embodiment 1, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing, preferably phthalic anhydride.

Embodiment 3: The method of embodiments 1 or 2, wherein the exchange catalyst comprises a ($C_{1-20}$ alkyl)-substituted amine, preferably a tri($C_{1-20}$ alkyl)amine more preferably triethylamine, trimethylamine, or a combination comprising at least one of the foregoing.

Embodiment 4: The method of any one or more of embodiments 1 to 3, wherein the initial molar ratio of phthalic anhydride to aromatic diimide is 4:1 to 20:1, or 4:1 to 10:1, or 4:1 to 8:1, or 4:1 to 5.5:1.

Embodiment 5: The method of any one or more of embodiments 1 to 4, wherein the initial molar ratio of amine exchange catalyst to the phthalic anhydride is 1:1 to 2:1.

Embodiment 6: The method of any one or more of embodiments 1 to 5, wherein the aqueous reaction mixture further comprises at least one of the aromatic diimide and the substituted or unsubstituted phthalic anhydride.

Embodiment 7: The method of any one or more of embodiments 1 to 6, wherein the aromatic diimide is of the formula

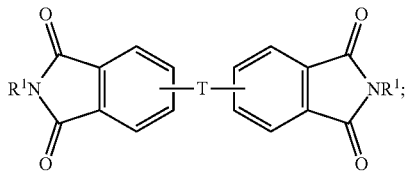

the aromatic tetra acid salt is of the formula

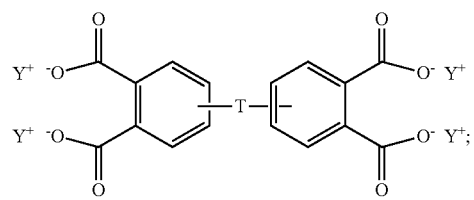

the aromatic triacid salt is of the formula

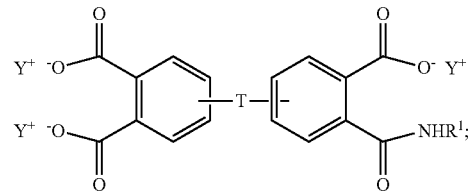

the aromatic imide-diacid salt is of the formula

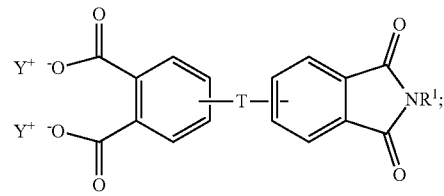

the aromatic dianhydride is of the formula

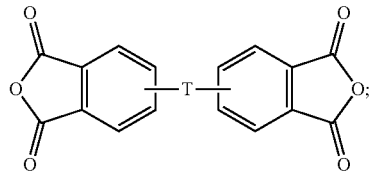

and
an aromatic imide-anhydride is of the formula

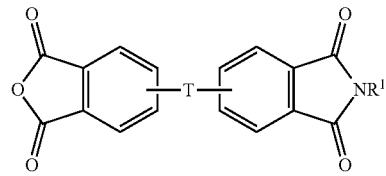

wherein in the foregoing formulas T is —O—, —S—, —C(O)—, —$SO_2$—, —SO—, —$C_yH_{2y}$— wherein y is an integer from 1 to 5 or a halogenated derivative thereof or —O—Z—O—, wherein Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing; $R^1$ is a monovalent $C_{1-13}$ organic group; and Y is a cationic group, preferably a $C_{1-20}$ trialkylammonium group or a proton, more preferably a $C_{1-20}$ trialkylammonium group.

Embodiment 8: The method of embodiment 7, wherein Z is a divalent group of the formula

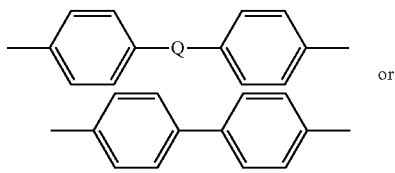

or wherein Q is —O—, —S—, —C(O)—, —SO$_2$—, —SO—, —P($R^a$)(=O)— wherein $R^a$ is a $C_{1-8}$ alkyl or $C_{6-12}$ aryl, or —$C_yH_{2y}$— wherein y is an integer from 1 to 5 or a halogenated derivative thereof, preferably wherein Z is 2,2-(4-phenylene)isopropylidene; and $R^1$ is a $C_{1-4}$ alkyl, preferably methyl.

Embodiment 9: The method of any one or more of embodiments 1 to 8 wherein the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

Embodiment 10: The method of any one or more of embodiments 1 to 9, wherein the organic solvent comprises toluene, xylene, chlorobenzene, ortho-dichlorobenzene, or a combination comprising at least one of the foregoing.

Embodiment 11: The method of any one or more of embodiments 1 to 10, wherein the volumetric ratio of the aqueous medium to the organic solvent is 0.3:1 to 3:1.

Embodiment 12: The method of any one or more of embodiments 1 to 11, wherein the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing; and an organic stream comprising the organic solvent, N-substituted phthalimide, and optionally unreacted aromatic diimide.

Embodiment 13: The method of any one or more of embodiments 1 to 12, wherein at least 50%, at least 70%, at least 80%, or at least 90% of the phthalimide in the aqueous reaction mixture at the beginning of the first time period is extracted into the organic solvent at the end of the first time period.

Embodiment 14: The method of any one or more of embodiments 1 to 13, wherein conversion of the aromatic diimide to the aromatic dianhydride is greater than 70%, or greater than 75%, or greater than 78%, or greater than 80% at the end of the second time period.

Embodiment 15: The method of any one or more of embodiments 1 to 14 wherein the method further comprises repeating the extracting to provide conversion of the aromatic diimide to the aromatic dianhydride at the end of the second time period of greater than 70%, or greater than 75%, or greater than 78%, or greater than 80%.

Embodiment 16: The method of any one or more of embodiments 1 to 15, wherein the method is a batchwise method.

Embodiment 17: The method of any one or more of embodiments 1 to 15, wherein the method is a continuous method.

Embodiment 18: The method of any one or more of embodiments 1 to 17, wherein the extracting for the first time period and the second time period are in the same extractor.

Embodiment 19: The method of any one or more of embodiments 1 to 17, wherein the extracting for the first time period and the second time period are in different extractors.

Embodiment 20: The method of any one or more of embodiments 1 to 19, wherein the reaction temperature is 160 to 200° C.; the first extraction temperature is 60 to 150° C.; and the second extraction temperature is 160 to 200° C.

Embodiment 21: The method of embodiment 1, wherein the reaction temperature is 160 to 200° C.; the first extraction temperature is 60 to 150° C.; the second extraction temperature is 160 to 200° C.; the aromatic diimide is of the formula

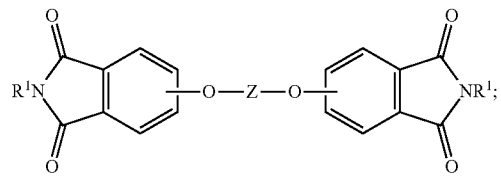

the aromatic tetra acid salt is of the formula

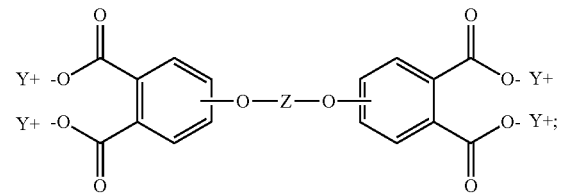

the aromatic triacid salt is of the formula

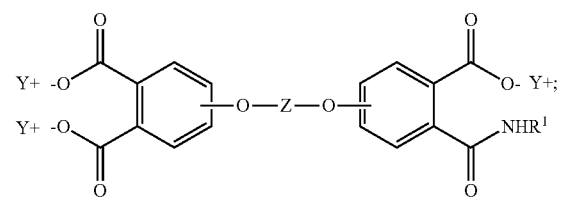

the aromatic imide-diacid salt is of the formula

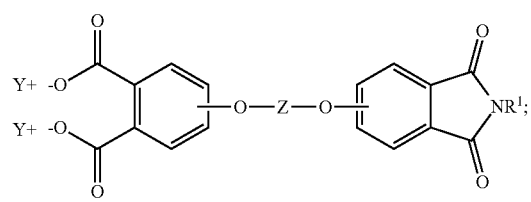

the aromatic dianhydride is of the formula

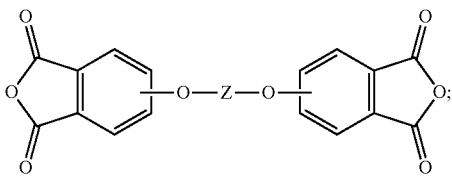

and
an aromatic imide-anhydride is of the formula

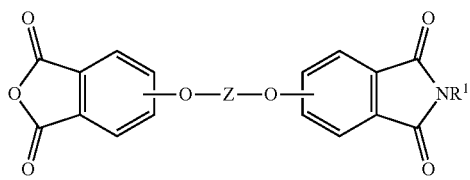

wherein in the foregoing formulas Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, preferably wherein Z is 2,2-(4-phenylene)isopropylidene; $R^1$ is a monovalent $C_{1-4}$ organic group, preferably wherein $R^1$ is a methyl group; and Y is a tri($C_{1-20}$ alkyl)ammonium group or a proton, preferably a triethylammonium group.

Embodiment 22: An aromatic dianhydride prepared by the method of any one or more of embodiments 1 to 21.

Embodiment 23: The aromatic dianhydride of embodiment 22, wherein the aromatic dianhydride has an imide anhydride content of less than or equal to 6 wt %, preferably less than or equal to 3 wt. %, more preferably less than or equal to 1 wt. %, even more preferably less than or equal to 0.1 wt %, based on the total weight of the aromatic dianhydride.

In general, the methods and aromatic dianhydrides can alternatively comprise, consist of, or consist essentially of, any appropriate components or steps herein disclosed. The methods and aromatic dianhydrides can additionally, or alternatively, be formulated so as to be devoid, or substantially free, of any components, materials, ingredients, adjuvants or species used in the prior art compositions or that are otherwise not necessary to the achievement of the function and/or objectives of the present claims.

All ranges disclosed herein are inclusive of the endpoints, and the endpoints are independently combinable with each other. "Or" means "and/or." "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. Reference throughout the specification to "another embodiment," "an embodiment," and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

The term "alkyl" means a branched or straight chain, saturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P.

"Substituted" means that the compound or group is substituted with at least one (e.g., 1, 2, 3, or 4) substituents instead of hydrogen, where each substituent is independently nitro (-NO$_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g, benzyl), $C_{7-12}$ alkylarylene (e.g, toluyl), $C_{4-12}$ heterocycloalkyl, $C_{3-12}$ heteroaryl, $C_{1-6}$ alkyl sulfonyl (-S(=O)$_2$-alkyl), $C_{6-12}$ arylsulfonyl (-S(=O)$_2$-aryl), or tosyl (CH$_3$C$_6$H$_4$SO$_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituents.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for producing an aromatic dianhydride, the method comprising
reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 150 to 300 psig;

removing the phthalimide from the aqueous reaction mixture by extracting the aqueous reaction mixture with an organic solvent for a first time period, at a first extraction temperature that is 60 to 160° C., provided that the first extraction temperature is at least 10° C. lower than a maximum of the reaction temperature;

subsequent to the first time period, extracting the aqueous reaction mixture with an organic solvent for a second time period, at a second extraction temperature that is 140 to 250° C., provided that the second extraction temperature is at least 5° C. higher than the first extraction temperature; and converting the aromatic tetraacid salt to the corresponding aromatic dianhydride.

2. The method of claim 1, wherein the substituted or unsubstituted phthalic anhydride is phthalic anhydride, 3-halophthalic anhydride, 4-halophthalic anhydride, 3-nitrophthalic anhydride, 4-nitrophthalic anhydride, or a combination of the foregoing.

3. The method of claim 1, wherein the exchange catalyst is a ($C_{1-20}$ alkyl)-substituted amine.

4. The method of claim 1, wherein the initial molar ratio of phthalic anhydride to aromatic diimide is 4:1 to 5.5:1.

5. The method of claim 1, wherein the initial molar ratio of amine exchange catalyst to the phthalic anhydride is 1:1 to 2:1.

6. The method of claim 1, wherein the aqueous reaction mixture further comprises at least one of the aromatic diimide and the substituted or unsubstituted phthalic anhydride.

7. The method of claim 1 wherein
the aromatic diimide is 4,4'-bisphenol A-bis-N-methylphthalimide, 3,4'-bisphenol A-bis-N-methylphthalimide, 3,3'-bisphenol A-bis-N-methylphthalimide, or a combination of the foregoing; and
the aromatic dianhydride is 4,4'-bisphenol A-bis-dianhydride, 3,4'-bisphenol A-bis-dianhydride, 3,3'-bisphenol A-bis-dianhydride, or a combination of the foregoing.

8. The method of claim 1, wherein the organic solvent is toluene, xylene, chlorobenzene, ortho-dichlorobenzene, or a combination of the foregoing.

9. The method of claim 1, wherein the volumetric ratio of the aqueous medium to the organic solvent is 0.3:1 to 3:1.

10. The method of claim 1, wherein the extracting provides
an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing; and
an organic stream comprising the organic solvent, N-substituted phthalimide, and optionally unreacted aromatic diimide.

11. The method of claim 1, wherein at least 50% of the phthalimide in the aqueous reaction mixture at the beginning of the first time period is extracted into the organic solvent at the end of the first time period.

12. The method of claim 1, wherein conversion of the aromatic diimide to the aromatic dianhydride is greater than 70% at the end of the second time period.

13. The method of claim 1 wherein the method further comprises repeating the extracting to provide conversion of the aromatic diimide to the aromatic dianhydride at the end of the second time period of greater than 70%.

14. The method of claim 1, wherein the method is a batchwise method.

15. The method of claim 1, wherein the method is a continuous method.

16. The method of claim 1, wherein the extracting for the first time period and the second time period are in the same extractor.

17. The method of claim 1, wherein the extracting for the first time period and the second time period are in different extractors.

18. The method of claim 1, wherein
the reaction temperature is 160 to 200° C.;
the first extraction temperature is 60 to 150° C.; and
the second extraction temperature is 160 to 200° C.

19. The method of claim 1, wherein
the reaction temperature is 160 to 200° C.;
the first extraction temperature is 60 to 150° C.;
the second extraction temperature is 160 to 200° C.;
the aromatic diimide is of the formula

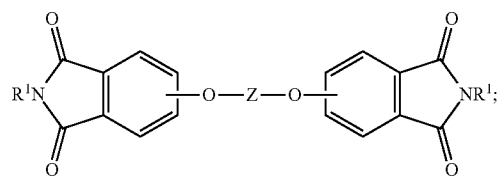

the aromatic tetra acid salt is of the formula

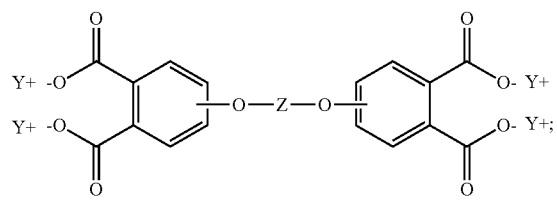

the aromatic triacid salt is of the formula

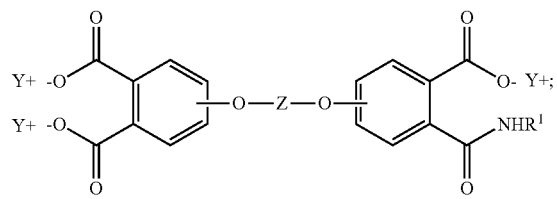

the aromatic imide-diacid salt is of the formula

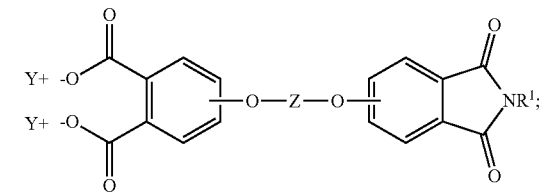

the aromatic dianhydride is of the formula

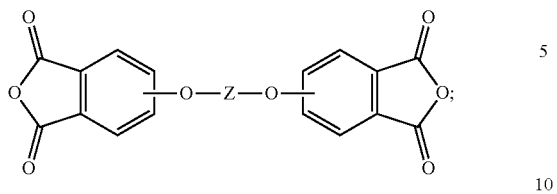

and
an aromatic imide-anhydride is of the formula

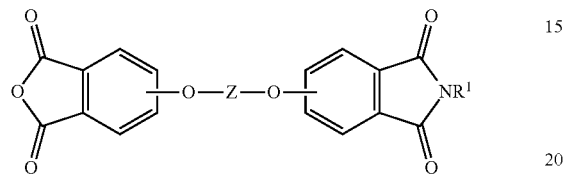

wherein in the foregoing formulas
- Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing;
- $R^1$ is a monovalent $C_{1-4}$ organic group; and
- Y is a tri($C_{1-20}$ alkyl)ammonium group or a proton.

20. The method of claim 1, wherein the aromatic dianhydride has an imide anhydride content of less than or equal to 3 wt %, based on the total weight of the aromatic dianhydride.

* * * * *